US007321829B2

(12) United States Patent
Remacle et al.

(10) Patent No.: US 7,321,829 B2
(45) Date of Patent: Jan. 22, 2008

(54) METHOD FOR THE IDENTIFICATION AND/OR THE QUANTIFICATION OF A TARGET COMPOUND OBTAINED FROM A BIOLOGICAL SAMPLE UPON CHIPS

(75) Inventors: José Remacle, Malonne (BE); Joseph Demarteau, Namur (BE); Nathalie Zammatteo, Jambes (BE); Isabelle Alexandre, Lesve (BE); Sandrine Hamels, Loverval (BE); Yves Houbion, Floreffe (BE); Francoise De Longueville, Jambes (BE)

(73) Assignee: Eppendorf Array Technologies (E.A.T.), Namur (BE)

( * ) Notice: Subject to any disclaimer, the term of this patent is extended or adjusted under 35 U.S.C. 154(b) by 0 days.

(21) Appl. No.: 09/574,626

(22) Filed: May 19, 2000

(65) Prior Publication Data

US 2003/0124522 A1    Jul. 3, 2003

(30) Foreign Application Priority Data

May 19, 1999   (EP)   .................................. 99870106
Feb. 18, 2000  (EP)   .................................. 00870025

(51) Int. Cl.
  G01N 33/48   (2006.01)
  G01N 25/20   (2006.01)
  C12Q 1/68    (2006.01)
  C12Q 33/567  (2006.01)
  C12Q 1/42    (2006.01)

(52) U.S. Cl. ........................... 702/19; 435/6; 435/7.21; 435/7.9; 435/21; 422/50; 702/20

(58) Field of Classification Search .................. 435/6, 435/7.21, 7.9, 21, 28, 7.2; 702/19, 20; 422/50
See application file for complete search history.

(56) References Cited

U.S. PATENT DOCUMENTS

| 4,244,797 | A | | 1/1981 | Aladjem et al. ............. 436/516 |
| 4,244,803 | A | | 1/1981 | Aladjem et al. ......... 422/82.01 |
| 5,486,452 | A | | 1/1996 | Gordon et al. |
| 5,646,001 | A | * | 7/1997 | Terstappen et al. ......... 435/7.21 |
| 5,744,305 | A | | 4/1998 | Fodor et al. |
| 5,807,522 | A | * | 9/1998 | Brown et al. .................. 422/50 |
| 5,902,727 | A | * | 5/1999 | Roth et al. ................. 435/7.21 |
| 6,027,890 | A | * | 2/2000 | Ness et al. ...................... 435/6 |
| 6,060,327 | A | | 5/2000 | Keen |
| 6,228,575 | B1 | * | 5/2001 | Gingeras et al. ................ 435/5 |
| 6,344,316 | B1 | * | 2/2002 | Lockhart et al. ................ 435/6 |
| 6,420,179 | B1 | | 7/2002 | Schultz et al. |
| 6,506,564 | B1 | | 1/2003 | Mirkin et al. |
| 2002/0177144 | A1 | | 11/2002 | Remacle et al. |

FOREIGN PATENT DOCUMENTS

| EP | 0 063 810 | | 11/1982 |
| EP | 0 267 521 A2 | | 5/1988 |
| EP | 0 619 321 A1 | | 12/1994 |
| EP | 0 646 784 A1 | | 4/1995 |
| EP | 7 179 180 | | 2/2002 |
| WO | WO 89/11548 | | 11/1989 |
| WO | WO90/15070 | | 12/1990 |
| WO | WO92/10588 | | 6/1992 |
| WO | WO94/19767 | | 9/1994 |
| WO | WO95/11995 | | 5/1995 |
| WO | WO96/15223 | | 5/1996 |
| WO | WO97/10365 | | 3/1997 |
| WO | WO97/21090 | | 6/1997 |
| WO | WO 98/04740 | | 2/1998 |
| WO | WO99/35499 | | 7/1999 |

OTHER PUBLICATIONS

Abouzied et al., Journal of AOAC International, vol. 77, No. 2 (Mar.-Apr.), pp. 495-501, 1994.*
Chen, J.J. et al. (1998) "Profiling expression patterns and isolating differentially expressed genes by cDNA microarray system with colorimetry detection" Genomics 51:313-324.
Duggan, D.J. et al. (1999) "Expression profiling using cDNA microarrays" Nature Genetics Supplement 21:10-14.
Ridley, S.M. et al. (1998) "High-throughput screening as a tool for agrochemical discovery: automated synthesis, compound input, assay design and process management" Pestic. Sci. 54:327-337.
Danscher et al., (1983) *Light Microscopic Visualization of Colloidal Gold on Resin-embedded Tissue*, The Journal of Histochemistry and Cytochemistry, vol. 31, No. 12, pp. 1394-1398.
Hayat, M.A. (1995) *Immunogold-Silver Staining, Principles, Methods, and Applications*, pp. 1-8, 40, 87-92.
Hauser-Kronberger et al., (1995) *Nonmicroscopical Colloidal Gold Autometallography (AMG$_{au}$): Use of Immunogold-Silver Staining in Blot Staining and Immunoassay*; immunigold-Silver Staining: Methods and Applications, pp. 289-296.
Erlich et al., (1991) *HLA-DR DQ and DP Tyoing Using PCR Amplification and Immobilized Probes*, European Journal of Immunogenetics, vol. 18; p.p 33-55.
Moeremans et al., (1984) *Sensitive Visualization of Antigen-Anitbody Reactions in Dot and Blot Immune Overlay Assays with Immunogold and Immunogold/Silver Staining*, Journal of Immunological Methods, vol. 74; pp. 353-360.

(Continued)

Primary Examiner—Shubo (Joe) Zhou
(74) Attorney, Agent, or Firm—Knobbe, Martens, Olson & Bear, LLP

(57) ABSTRACT

The present invention is related to a method for the identification and/or the quantification of a target compound obtained from a sample, preferably a biological sample, comprising the steps of putting into contact the target compound with a capture molecule in order to allow a specific binding between the target compound with a capture molecule, the capture molecule being fixed upon a surface of a solid support according to an array comprising a density of at least 20 discrete regions per cm$^2$, each of the discrete regions being fixed with one species of capture molecules, performing a reaction leading to a precipitate formed at the location of the binding, determining the possible presence of precipitate(s) in discrete region(s), and correlating the presence of the precipitate(s) at the discrete region(s) with the identification and/or a quantification of the target compound.

32 Claims, 7 Drawing Sheets

OTHER PUBLICATIONS

Cremers et al., (1987) *Non-radioactive in situ hybridization*, Histochemistry vol. 86, pp. 609-615.

Boege et al., (1996) *Selected Novel Flavones Inhibit the DNA Binding or the DNA Religation Step of Eukaryotic Topoisomerase I\**, The Journal of Biological Chemistry, vol. 271, No. 4, pp. 2262-2270.

Eliaou et al., (1992) *Generic HLA-DRB1 Gene Oligotyping by a Nonradioactive Reverse Dot-Blot Methodology*, Human Immunology, vol. 35, pp. 215-222.

Bassell, G.J. et al. (1994) "Single mRNAs visualized by ultrastructural *in situ* hybridization are principally localized at actin filament intersections in fibroblasts" *J. Cell Biol.* 126:863-876 (document O29 from the European opposition proceedings in the related European patent EP 1 179 180).

Brada, D. et al., (1984) "Golden Blot" - Detection of polyclonal and monoclonal antibodies bound to antigens on nitrocellulose by protein A - gold complexes *Analyt. Biochem.* 142:79-83 (document O32 from the European opposition proceedings in the related European patent EP 1 179 180).

Danscher, G. (1981) "Light and electron microscopic localization of silver in biological tissue" *Histochemistry* 71:177-186 (document O33 from the European opposition proceedings in the related European patent EP 1 179 180).

Danscher, G. (1981) "Localization of gold in biological tissue - a photochemical method for light and electronmicroscopy" *Histochemistry* 71:81-88 (document O34 from the European opposition proceedings in the related European patent EP 1 179 180).

De Blas, A.L. et al., (1983) "Detection of antigens on nitricellulose paper immunoblots with monoclonal antibodies" *Anal. Biochem.* 133:214-219 (document O66 from the European opposistion proceedings in the related European patent EP 1 179 180).

Gordon, J. Expert Opinion Aug. 23, 2005, in 4 pages (document O63 from the European opposition proceedings in the related European patent EP 1 179 180).

Gu, J. et al. (1995) "Quantitative evaluation of immunogold-silver staining" Chapter 7, *Immunogold-Silver Staining: Methods and Applications*, pp. 119-136 (document O36 from the European opposistion proceedings in the related European patent EP 1 179 180).

Hacker, G.W. (Jul. 28, 2005) Expert's Opinion (documents O30 in German and 030a English translation, from the European opposition proceedings in the related European patent EP 1 179 180).

Hacker, G.W. et al. (1997) "Immunogold-silver staining - autometallography: recent developments and protocols" *Analytical Morphology: Theory, Applications & Protocols*, Ed. Jiang Gu, Eaton Publishing, Chapter Two, pp. 41-54, A-3, A-2 (document O46 from the European opposition proceedings in the related European patent EP 1 179 180).

Hacker, G.W. et al. (1996) "Electron microscopical automet-lography: immunogold-silver staining (IGSS) and heavy-metal histochemistry" Methods: A Companion to Methods in Enzymology 10:257-269 (document O45 from European opposition proceedings in the related European patent EP 1 179 180).

Hacker, G.W. et al. (1995) "Autometallography and its use in electron microscopy" BEDO 26:129-143 (document O39 from the European opposition proceedings in the related European patent EP 1 179 180).

Hacker, G.W., et al. (1995) "Immunogold-silver staining detection of *in situ* molecular biological reaction sites" Proceedings 3rd International Conference and Workshops, Modern Methods in Analytical Morphology, pp. 64-70 (document O42 from the European opposition proceedings in the related European patent EP 1 179 180).

Hacker, G.W. et al. (1995) "Immunogold-silver staining detection of *in situ* molecular biological reaction sites" Cell Vision 2:247-253 (document O44 from the European opposition proceedings in the related Euopean patent EP 1 179 180).

Hacker, G.W. et al. (1995) "Silver staining techniques, with special reference to the use of different silver salts in light and electron microscopical immunogold-silver staining" *Immunogold-Silver Staining: Methods and Applications*, Chapter Two, pp. 20-45 (document O43 from the European opposition proceedings in the related European patent EP 1 179 180).

Hacker, G.W. et al. (1994) "Detection of nucleic acids by immunogold-silver staining (IGSS), Fluorescent-, peroxidase- and alkaline phosphatase-based methods " *Cell Vision* 1:71-73 (document O40 from the European opposition proceedings in the related European patent EP 1 179 180).

Hacker, G.W. et al. (1994) "*In situ* detection of DNA and mRNA sequences by immunogold-silver staining (IGSS)" *Cell Vision* 1:30-38 (document O41 from the European opposition proceedings in the related European patent EP 1 179 180).

Hacker, G.W. et al. (1988) "Silver acetate autometallography: an alternative enhancement technique for immunogold-silver staining (IGSS) and silver amplification of gold, silver, mercury and zinc in tissues" *J. Histotechnol.* 11:213-221 (document O38 from the European opposition proceedings in the related European patent EP 1 179 180).

Hacker, G.W. et al. (1985) "The immunogold-silver staining method: a powerful tool in histopathology", *Virchows Arch. (Pathol. Anat.)* 406:449-461 (document O37 from the European opposition proceedings in the related European patent EP 1 179 780).

Hainfeld J.F. et al. (1993) "High-resolution gold labeling" *Proc. 51st Annual Meeting of the Microscopy Society of America*, (Eds. G.W. Bailey and C.L. Rieder), published by San Fancisco Press, Inc, pp. 330-331 (document O47 from the European opposition proceedings in the related European patent EP 1 179 180).

Holgate, C.S. et al. (1983) "Immunogold-silver staining: new method of immunostaining with enhanced sensitivity" *J. Histochem. Cytochem.* 31:938-944 (document O50 from the European opposition proceedings in the related European patent EP 1 179 180).

Holgate, C.S. et al. (1983) "Surface membrane staining of immunoglobulins in paraffin sections of non-hodgkin's lymphomas using immunogold-silver staining technique" *J. Clin, Pathol.* 36:742-746 (document O49 from the European opposition proceedings in the related European patent EP 1 179 180).

Jones, A. et al. (1988) "Colloidal gold for the detection of proteins on blots and immunoblots" *Methods Molecul.r Biol* 3:441-479 (document O51 from the European opposition proceedings in the related European patnet EP 1 179 180).

Kronberger, C.H. et al. (1995) "Nonmicroscopical colloidal gold autometallography ($AMG_{Au}$): use of immunogold-silver staining in blot staining and immunoassay" *Immunogold-Silver Staining: Methods and Applications*, Chapter 19, pp. 289-297 (document O48 from the European opposition proceedings in the related European patent EP 1 179 180).

Lackie, P.M. et al. (1985) "Investigation of immunogold-silver staining by electron microscopy" *Histochemstry* 83:545-550 (document O52 from the European opposition proceedings in the related European patent EP 1 179 180).

Larson, G. (1992) "Stabilized TMB substrate for horseradish peroxidase vs. 4-chloro-1-naphthol: a comparison on Western blots" Promega Notes Magazine 39:17., EP 00929132.9-2404 (document O17 from the European opposition poceedings in the related European patent EP 1 179 180).

Moermans, M. et al. (1985) "Sensitive colloidal metal (gold or silver) staining of protein blots on nitrocellulose membranes" *Anal. Biochem.* 145:315-321 (document O54 from the European opposition proceedings in the related European patent EP 1 179 180).

Nespolo, A. et al. (1989) "Immunoblotting techniques with pictogram sensitivity in cerebrospinal fluid protein detection" *Electrophoresis* 10:34-40 (document O55 from the European opposition proceedings in the related European patent EP 1 179 180).

Patel, N. et al. (1991) "A silver enhanced, gold labeled, immunosorbent assay for detecting antibodies to rubella virus" *J. Clin. Pathol.* 44:334-338 (document O56 from the European opposition proceedings in the related European patent EP 1 179 180).

Patel, N. et al. (1992) "Direct measurement of low density lipoprotein in whole blood by silver-enhanced gold-labelled immunoassay" *Ann. Clin. Biochem.* 29:283-286 (document O57 from the European opposition proceedings in the related European patent EP 1 179 180).

Patel, N. et al. (1993) "Sandwich silver enhanced gold labeled immunosorbent assay for determination of human growth hormone" *J. Histotechnol.* 16:259-261 (document O58 from the European opposition proceedings in the related European patent EP 1 179 180).

Rufner, R. et al. (1994) "Detection of atrial natriuretic peptides (ANP) in rat atria by immunogold-silver staining (IGSS)" *Proc. 52nd Annual Meeting of the Microscopy Society of America*, (G.W. Bailey and A.J. G. Arratt-Reed, Eds.), published by San Francisco Press, Inc. (document O59 from the European opposition proceedings in the related European patent EP 1 179 180).

Rufner, R. et al. (1995) "Autometallography for immunogold-silver staining in light and electron microscopy" *Cell Vision* 2:327-333 (document O60 from the European opposition proceedings in the related European patent EP 1 179 180).

Schofer, C. et al. (1997) "High resolution detection of nucleic acids at the electron microscopic level - review of in situ hybridization technology, the use of gold, and catalyzed reporter deposition (CARD)" *Cell Vision* 4:443-454 (document O62 from the European opposition proceedings in the related Eurpopean patent EP 1 179 180).

Scippo, M.L. et al. (1989) "A non-radioactive method to detect RNA or DNA using an oligonucleotide probe with bromodeoxyuridine free ends, a monoclonal antibody against bromodeoxyurdine and immunogold silver staining" *Arch. Int. Physiol. Biochim.* 97:279-284 (document O61 from the European opposition proceedings in the related European patent EP 1 179 180).

Spezialetti, R. et al. (1997) Annual Meeting Abstracts in 1 page, presented at the U.S. & Canada Ac. Pathol., No. 1082, (document O31 from the European opposition proceedings in the related European patent EP 1 179 180).

Springall, D.R. et al. (1984) "The potential of the immunogold-silver staining method for paraffin sections" *Histochemistry* 81:603-608 (document O53 from the European opposition proceedings in the related European patent EP 1 179 180).

Towbin, H. et al. (1979) "Electrophoretic transfer of proteins from polyacrylamide gels to nitrocellulose sheets: procedure and some applications" *PNAS USA* 76:4350-4354 (document O64 from the European opposition proceedings in the related European patent EP 1 179 180).

Towbin, H. et al. (1984) "Immunoblotting and dot immunobinding - current status and outlook" *J. Immunol. Methods* 72:313-340 (document O65 from the European opposition proceedings in the related European patent EP 1 179 180).

Varndell, I.M. (1984) "Visualisation of messenger RNA directing peptide synthesis by *in situ* hybridization using a novel single-stranded cDNA probe" *Histochemsirty* 81:597-601 (document O35 from the European opposition proceedings in the related European patent EP 1 179 180).

U.S. Appl. No. 09/240,775 filed Jan. 29, 1999, Mirkln et al.

U.S. Appl. No. 09/344,667 filed Jun. 25, 1999, Mirkin et al.

Ridley, S.M. et al. (1998) "High-throughput screening as a tool for agrochemical discovery: automated synthesis, compound input, assay design and process management" *Pestic.Sci.* 54:327-337.

Speel, E. (1999) "Detection and amplification systems for sensitive, multiple-target DNA and RNA in situ hybridization: looking inside cells with a spectrum of colors" *Histochem. Cell Biol.* 112:89-113.

\* cited by examiner

METHOD FOR THE IDENTIFICATION AND/OR THE QUANTIFICATION OF A TARGET COMPOUND OBTAINED FROM A BIOLOGICAL SAMPLE UPON CHIPS

This application claims priority of European application 99870106.4, filed May 19, 1999, and European application 00870025.4, filed Feb. 18, 2000.

FIELD OF THE INVENTION

The present invention is related to a method for the identification and/or the quantification of a target compound obtained from a biological sample by binding to a capture molecule fixed upon chips.

The present invention is also related to an identification and/or quantification apparatus based upon said method, that allows the identification and/or the quantification of positive locations of bounded target compounds upon said chips

BACKGROUND ON THE INVENTION AND STATE OF THE ART

Biological assays are mainly based upon interaction specificity between two biological molecules such two strands of nucleic acid molecules, an antigen and an antibody or a ligand and its receptor. The present challenge of biological assays is to perform simultaneously the multiple detection of molecules present in a sample. Miniaturisation and development of arrays upon the surface of "biochips" are tools that allow multiplex reactions in a microscopic format, said detection being made with a limited volume of sample for the screening and/or the identification of multiple possible target compounds. These arrays are formed of discrete regions, containing a specific capture molecule used for the binding of the target compound. These discrete regions, as small as a few micrometers, allow the fixation of several thousands capture molecules per $cm^2$ surface (WO 95/11995).

However, the detection of bounded target compounds is difficult, since their amount is very small due to said miniaturisation (few fentomoles or even few attomoles). Therefore, only extremely sensitive methods are adequate for such detection.

It has been proposed a labelling of a target compound like DNA with fluorescent molecules after their possible genetic amplification. When an RNA molecule has to be detected, it is first transformed into a cDNA, before its possible amplification. If direct labelling of the target compound is not possible, a double reaction (sandwich reaction) can be performed. However, the amount of fluorescent molecules is so low that it is necessary to develop specific array scanners for the detection and/or the quantification of the bounded compound upon the "hybridisation chips". Said expensive specific scanners comprise a laser scanner for excitation of the fluorescent molecules, a pinhole for decreasing the noise fluorescent background, and a photomultiplier for increasing the sensitivity of the detection, Alternative detection methods that present a high sensitivity are described in the documents U.S. Pat. No. 5,821,060 and WO95/04160 and are based upon the detection using expensive devices such as mass spectrometers It has also been proposed methods based upon the precipitation of specific products resulting of a calorimetric labelling (U.S. Pat. Nos. 5,270,167, 4,731,325, EP-A-0301141) or the result of an enzymatic activity (EP-A-0393868, WO 86/02733, EP-A-0063810). However, said methods are either characterized by a low sensitivity or are not adequate for the detection of a target compound upon "hybridisation chips", because the precipitate will occur at a certain distance of the reaction binding and its location can not be easily correlated with a specific bounded target compound. In addition, the density of the precipitate of such enzymatic reactions is not enough opaque for allowing a detection by light absorption.

It has also been proposed to improve the detection by fixing a soluble product obtained from the enzymatic reaction with a metal before its precipitation. However, as the result of said enzymatic reaction is a soluble product, there is no correlation between the location of the precipitate and the detection of a specific bounded target compound.

AIMS OF THE INVENTION

The present invention aims to provide a new identification and/or quantification method of one or more target compounds present (possibly simultaneously) in a biological sample and that will not present the drawbacks of the state of the art.

The present invention aims to provide such a method that is simple and not expensive, that allows the detection of said target compounds by using fixed capture molecules upon arrays of the surface of a solid support.

A last aim of the present invention is to provide also a simple and non-expensive apparatus based upon said method, that improves the identification and/or the quantification of bounded target compounds upon "hybridisation chips".

SUMMARY OF THE INVENTION

The present invention is related to a method for identification and/or quantification of at least one target compound present in a biological sample by its binding upon a capture molecule fixed upon arrays of a solid support (hereafter called "hybridisation chips"), the binding of said target compound upon its corresponding capture molecule resulting in the formation of a metal precipitate at the location of said capture molecule.

Advantageously, said method comprises the steps of:
putting into contact the target compound with a capture molecule in order to allow a specific binding between said target compound with a (corresponding) capture molecule, said capture molecule being fixed upon a surface of a solid support according to an array comprising at least a density of 20 discrete regions per $cm^2$, each of said discrete regions being fixed with one species of capture molecules, performing a reaction, preferably a (chemical or biochemical) catalytic reaction, leading to a formation of a precipitate at the location of said binding, determining the possible presence of a precipitate in a discrete region preferably by the use of a scanner, and correlating the presence of the precipitate(s) at the discrete region(s) (precipitate pattern) with the identification and/or a quantification of said target compound in the biological sample.

The "hybridisation chips" according to the invention are any kind of solid support that allow the formation of arrays of capture molecules (specific pattern) upon one or more of its surfaces. Said solid support can be made of glasses, filters, electronic device, polymeric or metallic materials, etc. Preferably, said arrays contain specific locations (advantageously presented according to a specific pattern), each of them containing normally only one species of capture molecule.

The fixation of DNA strands on proteins thereafter specifically attached to sites specific locations on a substrate, is described in the document U.S. Pat. No. 5,561,071. It is also known that capture chemicals can be linked to microtubes that are then spatially arranged in order to produce an array, as described in the document GB-3 319 838, or to obtain the direct synthesis of oligonucleotides on specific surfaces by using photolithographic techniques as described in the documents EP-0476014, U.S. Pat. Nos. 5,510,270, 5,445,934, WO97/29212, U.S. Pat. Nos. 5,605,662, 5,632,957 and WO94/22889.

All these methods for the fixation of capture molecules on the surface of a solid support in order to obtain the above-described arrays are compatible with the present invention.

The biological target compounds according to the invention may be present in a biological (or possibly a non-biological) sample such as clinical samples extracted from blood, urine, faeces, saliva, pus, serum, tissues, fermentation solutions or culture media. Said target compounds are preferably isolated purified, cleaved, copied and/or amplified if necessary by known methods by the person skilled in the art before their detection and/or quantification upon the "hybridisation chips".

Preferably, the formation of a precipitate at the location of the binding is obtained with the fixation of a metallic compound upon the bounded target compound or by the result of a reduction of a metal in the presence of an enzyme. Advantageously, a reduction of silver in the presence of colloidal gold allows the formation of a precipitate at a distance not exceeding few micrometers prom the bounded target compound to its capture molecule, According to the invention, the specific locations on the array are smaller than 1000 µm in length. These locations or spots have preferably a diameter comprised between 10 and 500 µm and are separated by distance of similar order of magnitude, so that the array of the solid support comprises between 100 and 250,000 spots upon the surface of 1 cm$^2$. However, it is also possible to prepare spots smaller as 1 µm or less upon which the capture molecules are fixed. The formation of said spots or locations would be obtained by known microelectronic or photolitographic processes and devices that allow the fixation of said capture molecules on the surface of the solid support either by a covalent linkage or a non-covalent adsorption. The covalent linkage technique is preferred in order to control specifically the sites of capture molecules fixation and avoid possible drawbacks that may result with several capture molecules (like nucleic acids or antibodies) that can be desorbed during incubation or washing step.

One of the preferred embodiment is the fixation of biological molecules like proteins, peptides or nucleic acid sequences by linkage of amino groups on activated glass bearing aldehyde moiety. The incorporation of an amine group in the nucleic acid chain is easily obtained using aminated nucleotide during their synthesis. Aminated amino acids can be fixed upon the surface of a solid support like glass bearing aldehyde groups as described by Schena et al. (Proc. Natl. Acad. Sci. USA, 93, pp. 10614–10619 (1996)) or as described in the document U.S. Pat. No. 5,605,662 and the publication of Krensky et al. (Nucleic Acids Research, 15, pp. 2891–2909 (1987)). The linkage between an amino and a carboxyl group is obtained by the presence of a coupling agent like carbodiimide compounds as described by Joos et al. (Anal. Biochem., 247, pp. 96–101 (1997)).

Thiol modified oligonucleotides can be used also to obtain a reaction with amino groups upon the surface of a solid support in the presence of cross-linking molecules (Thrisey et al., Nucleic Acids Research, 24, pp. 3031–3039 (1996)). Similarly, oligonucleotides can be fixed to a gel like polyacrylamide bearing hydroxyl and aldehyde groups as described in the document U.S. Pat. No. 5,552,270 and WO98/28444.

The binding (or recognition) of the target compound upon their corresponding specific capture molecules is a spontaneous non-covalent reaction when performed in optimal conditions It involves non-covalent chemical bindings. The medium composition and other physical and chemical factors affect the rate and the strength of the binding. For example for nucleotide strand recognition, low stringency and high temperature lower the rate and the strength of the binding between the two complementary strands. However, they also very much lower the non specific binding between two strands (which are not perfectly complementary) When several sequences are similar, the specificity of the binding can be enhanced by addition of a small amount of non-labelled molecules, which will compete with their complementary sequence, but much more with the other ones, thus lowering the level of cross-reactions.

The optimisation of the binding conditions is also necessary for antigen/antibody or ligand/receptors recognition, but they are usually rather specific.

A preferred embodiment of this invention is to take party of the amplification given by the catalytic reduction of Ag$^+$ in the contact of other metals like gold. Gold nanoparticules are currently available and they can be easily fixed to molecules like protein. For example, streptavidin coated gold particles are available on the market.

According to a preferred embodiment of this invention, one uses a labelled target molecule, which is then recognised by a conjugate. This labelled molecule (biotin, haptens, . . . ) can be considered as a first member of the binding pair. For DNA, the labelling is easily done by incorporation of biotinylated nucleotides during their amplification. For the RNA, biotinylated nucleotides are used for their copy in cDNA or thereafter in the amplification step. Amplification of the nucleotide sequences is a common practice since the target molecules are often present in very low concentrations. Proteins are easily labelled using NHS-biotin or other reactions. Once the biotinylated molecules are captured, a streptavidin-gold complex, which is the second member of the binding pair, is added and the streptavidin specifically recognises biotin, so that the complex is fixed at the location where the target is fixed. If haptens are used as label, an antibody-gold complex will be used. Then a reactive mixture containing A$^{30}$ and a reducing agent is added on the surface and Ag layers will precipitate on the gold particles leading to the formation of crystal particles.

Direct labelling of the target molecules with gold is possible by using gold-labelled antigens, antibodies or nucleotides.

An alternative is to avoid any labelling of the target molecule, and then a second nucleotide sequence is used which is labelled. They then formed a sandwich hybridisation or a sandwich reaction with the capture molecule fixing the target and the labelled nucleotide sequence, which allows the detection to go on. Like above, the labelled nucleotide sequence is able to catalyse itself the precipitation of the metal or it does it through a second complex.

The Ag precipitation corresponds to the location of the binding of biotinylated nucleotide sequence. As said location is well defined, it is possible to identify the presence of said precipitate (specific spot of the array).

The precipitate has the form of small crystals that reach with time a diameter of about 1 µm. The formation of these small crystals represents a real amplification of the signal since they originated from the presence of gold particles a few nm in diameter.

Unexpectedly, within a given range of labelled nucleotide sequences present on the surface, a concentration curve could be obtained between the gold-labelled nucleotide sequence concentration and the amount of precipitate on the surface. One constraint of the array is that the detection signal has to be correlated with the location where it originates.

Because of its granular form, the precipitate advantageously modifies the reflection of the light. It also leads to a strong diffusion of the light (spot detected), which is recordable by known detection means. Such diffusion assays are typically detected and recorded from the reflection of a light beam with photodiodes. One unexpected observation is that this assay for the presence of silver crystals was found unexpectedly very sensitive. The fact that the silver precipitate appears as a black surface allows the use of a scanner (absorption of the light through the transparent surface of the array). The presence of insoluble precipitate will absorb the light, which is then detected and recorded. The advantage of the scanner is that only a small portion of the array is detected at one time so that a much better resolution can be obtained. Either the illumination beam or the detection surface is focalised and the signal is recorded so that the image of the array can be reconstituted. The detection means (detector) can be a CCD or CMOS camera, which measures the overall array. The resolution of the detection is then dependent on the number of pixels of the camera. On the other end, the detector can be constituted of photo-diodes arranged into a line and the image is scanned by moving in front of this line. Scanners with a sensitivity of 11 µm for a pixel can be constructed, which are sufficient to analyse spots of 50 µm in diameter or bigger.

A full illumination of the array combined with a recording of the light transmitted is also possible (faster than the scanner, but seems to be less sensitive).

As a metal, silver is able to reflect light by itself. Even if the efficiency of this reflection is low, it exists and can be used in order to localise the silver precipitate (spots) Because of its metal nature, other methods like variations of an electromagnetic field or electric conductance are also possible.

Another aspect of the present invention concerns a diagnostic and/or quantification apparatus of one or more identical or different target compound(s) obtained from a sample, said apparatus comprising:
 a detection and/or quantification device of precipitates (spots) upon the surface of a solid support resulting from the binding of a target compound upon its corresponding capture molecule above-described,
 possibly a reading device of information(s) recorded upon said solid support (such as barcodes), and
 a computer programmed to:
  possibly recognise the discrete regions bearing capture molecules,
  collect the results obtained from said detection device, possibly correlated with the information(s) obtained from said reading device, and
  carry out a diagnostic and/or quantification of said target compound(s).

Hence, detection resolution, and more particularly the reliability of the final quantification depends largely on the characteristics of the detection device. Especially, when the detection device includes a CCD camera, the reliability depends on its number of pixels. The number of pixels thus limits the allowed sensitivity of the quantification. Typically, it is possible to obtain with a CCD a resolution of 10 µm for a pixel, which are sufficient to analyse spots of 100 µm in diameter or bigger. However, such quantification is limited by the number of pixels, by the resolution of each pixel and the fact that the sensitivity is given by only one view point. One view point depends on the three following patterns: the position of the lecture element like CCD camera, the position of the object to be detected and the position of the lightening of the object.

In order to respond to said objectives, the present invention is also related to a method (preferably dedicated to the detection and/or the quantification of a precipitate according to the invention, but not only to such precipitate) for the quantification of a volume of a precipitate (preferably containing metal crystals) upon a defined surface of a solid support, said defined surface of a solid support being defined by an array of at least 4, at least 10, at least 16, at least 20 or more discrete regions per $cm^2$ each discrete region possibly comprising a precipitate. According to the invention images of said defined surface comprising one or more precipitates correspond to different views, said images containing analogue informations being taken by one or several camera(s) and upon illumination by one or several illuminant source(s) being spatially arranged relatively to each other according to a predetermined pattern; the corresponding image analogue informations of said defined surface comprising said precipitate(s) being transformed and converted into digital form or set of digital forms and compared to a first and to a second reference standard to determine the volume of the precipitate(s) to be quantified.

The first reference standard corresponds to the digital form or set of digital forms obtained from analogue informations contained in images taken on said surface without precipitate.

The second reference standard corresponds to the digital form or set of digital forms obtained from analogue informations contained in images taken on said surface comprising precipitates of known volume.

The term "volume" should be understood to mean the volume for which it is desired to obtain dimensional-type information. In the present invention, said volume results from a chemical or biochemical reaction following a binding between a target compound and its corresponding compound. Therefore, said obtained volume is the expression of said chemical or biochemical reaction following a binding between a target compound and its corresponding capture compound.

The term "image" should be understood to mean a group of pixels which is an illustration of a measure of said volume and which may be directly transmitted to and registered upon a monitor such as a screen or a printer.

The present invention is also related to an apparatus comprising means for implementing said method, preferably comprising one or several sensor(s) provided with cameras and with one and/or several illuminant source(s) which are spatially arranged relatively to each other according to a predetermined pattern and which are associated with an analogue information acquisition system, the information being measured by using said sensors and being converted into digital form by a processing unit.

Preferably the transformation and conversion are made by a processing unit on board of the camera or in a computer.

The cameras are preferably mono, infrared, colour, special adjacent range CCD or CMOS cameras or similar lecture technologies.

The illuminant source is preferably an infrared light having a wavelength similar to the dimension of the metal crystals contained in the precipitate(s) and which is advantageously produced by using a single diode or diodes having the same spectral distribution.

The illuminant sources are advantageously regularly spaced around the solid support, each of said sources corresponding to a light spot, which can be automatically switched on simultaneously or successively.

The images are preferably obtained either by transparency, by reflection or by a combination thereof.

As illustrated in the enclosed drawings, the apparatus and method may comprise the use of one camera and one illuminant source, placed above the solid support, said camera and said illuminant source being movable in the three dimensions in space.

The apparatus and method may comprise also the use of two or more cameras oppositely arranged in a plane and placed above the solid support and one or more illuminant sources placed under the solid support.

The apparatus and method may comprise also the use of three or more cameras arranged according to a triangular plane or another regular or irregular pattern and placed above the solid support and one or more illuminant sources placed under the solid support.

The apparatus and method may comprise the use of one camera placed above the solid support, a first illuminant source placed above the solid support and under said camera, a second illuminant source placed under the solid support, the two illuminant sources being placed almost symmetrically according to the position of the solid support.

Alternative preferred embodiments of the present invention are based upon the use of one or more illuminant source(s) and one or more camera(s) which may be used according to the method of the present invention, either in combination or consecutively, said illuminant source(s) and/or said camera(s) can be maintained fixed during the lecture or can be moved according to a preferred translation or rotation movement along or around the solid support comprising the specific volume of a precipitate.

It is also possible by using one or more illuminant source(s) and/or one or more camera(s) to allow the movement of the solid support comprising a specific volume of a precipitate.

Other embodiments that may be used according to the invention are apparatus comprising (i) either one camera and several illuminant sources with the different illuminant sources arranged from each other according to different symmetric or non-symmetric patterns, (ii) or one illuminant source and several cameras, said cameras being arranged from each other according to different symmetric or non-symmetric patterns, (iii) or a combination thereof. The illuminant is an infrared light having a wavelength similar to the dimension of the crystals contained in the precipitate.

The person skilled in the art is also able to provide means for performing the various steps of the present invention, especially the transformation and the conversion of the major volume into digital form or a set of digital forms by using known means or methods such as the ones present in the software and computer technologies.

The present invention is also related to a computer program product (software), comprising program code means for performing all or part of the step of the method according to the invention, when said program is run on a computer.

The present invention is related to a computer program product comprising program code means stored on a computer readable medium for performing the method according to the invention, when said program product is run on a computer.

Said means are able to collect the results obtained from said detection and/or quantification device and possibly the information(s) obtained by said reading device, and said means are able to carry out a diagnostic and/or quantification of a specific target compound resulting from the analysis of said results, possibly correlated to the read information(s).

Said means of this computer program product are able to obtain a discrimination between the spots and a possible detected background noise, for instance by the identification of homogeneous parts of an image after having been merged into two classes used as training sets. This discrimination can be enhanced by post-classification contextual filters techniques.

Said means are also able to identify the contour of the spot itself, which will be superposed to the original image and will allow the measure of intensity level of the counted pixels identified in the spot.

The quantification means allow an integration of all pixels intensity present in the spot or a recording the overall level of intensity of the homogeneous parts of the spot.

Furthermore, these means allow a statistical comparative analysis between the spots of each sample and a control or reference standard (standard target compound) or between two or more spots (preferably with a correlation with the recorded information of the solid support). Image correlation could be obtained between the spot image and said standard target compound spot image in order to discriminate spots that are statistically different in one test compared to another.

The recorded signal(s) by the detection device and the reading device can be read, processed as electronically computerised data, analysed by said appropriate computer program product (software).

According to a specific embodiment of the present invention, the array bears fixed oligonucleotide capture nucleotide sequences so as to allow a detection, amplification and possibility quantification of nucleic acid sequences upon a same solid support. In an alternative form of execution, the array comprises fixed PCR primers in order to obtain the production of amplicons and fixation of amplicons upon the surface according to the method described by Rasmussen et al. (Anal. Biochem., 198, pp. 138–205 (1991)), which allows thereafter their detection.

The array according to this invention is used in a diagnostic kit, in a diagnostic and/or quantification apparatus which allows automatic lecture, possibly after a previous treatment, such as purification, cleaving, copying and/or genetic amplification.

Preferably, the detection and/or quantification apparatus according to the invention is a system that combines multiple steps or substeps within an integrated system as an automatic nucleic acid diagnostic system (the steps of purification of the nucleic acid sequences in a sample, of amplification (through known genetic amplification methods), the diagnostic and possibly the quantification).

Preferred embodiments of the present invention will be described in the following non-limiting examples in reference to the figures.

EXAMPLE 1

Detection of DNA on Biochips

Figure 1:
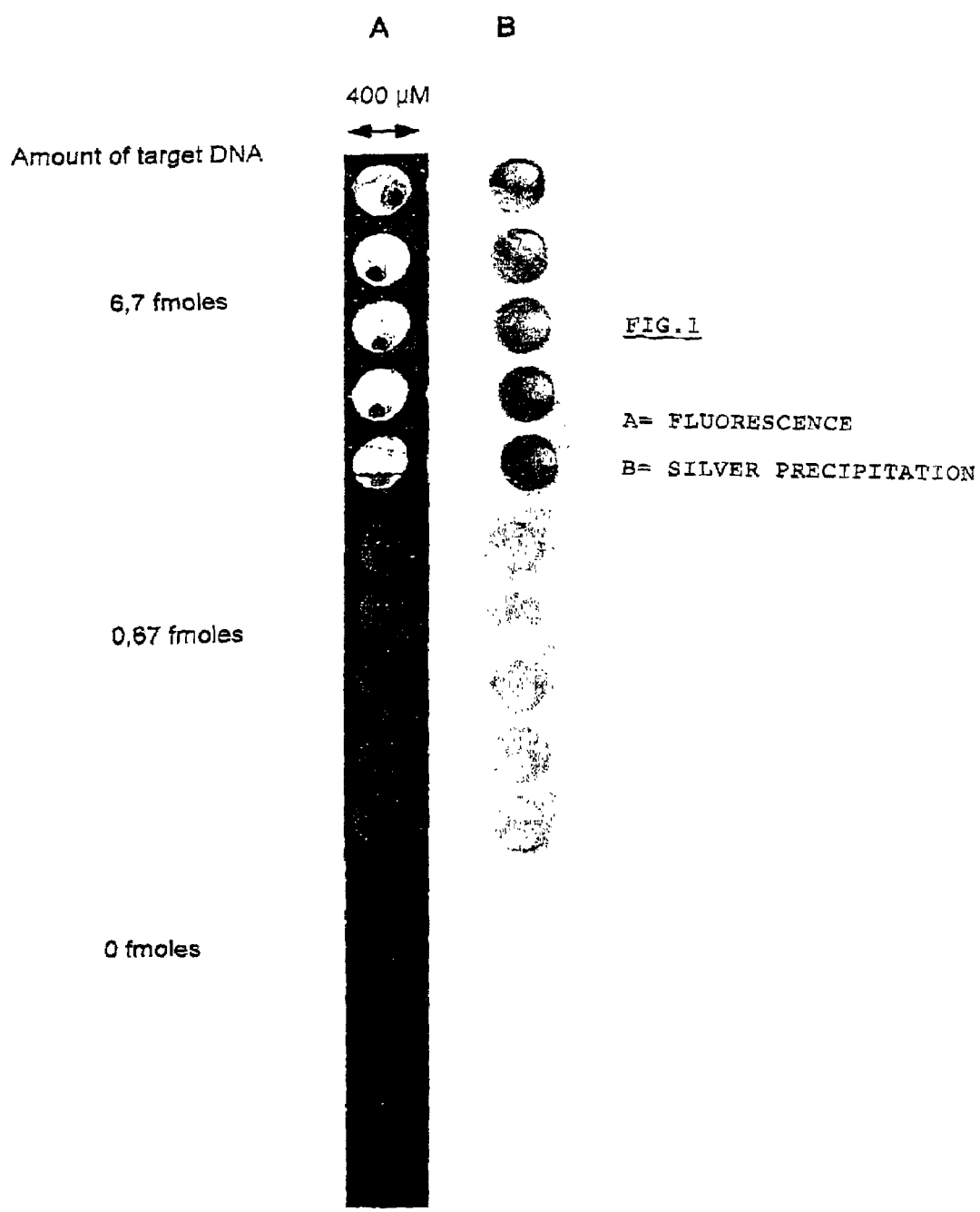
FIG. 1 compares the detection of target molecules obtained on arrays composed of DNA capture nucleotide sequences covalently fixed on glass and used to detect 3 concentrations of biotinylated target DNA either in fluorescence or after silver concentration.

In this experiment, target DNA labelled is detected by direct hybridisation on capture nucleotide sequences bound to the array. Capture nucleotide sequences were covalently bound on glass and direct hybridisation performed with complementary biotinylated DNA. The positive hybridization was detected with silver precipitate catalysed by the nanogold particles linked to streptavidin.

Binding of Capture Nucleotide Sequences on Glass

Activated glass bearing aldehyde groups were purchased from CEL Associates (USA). Aminated capture nucleotide sequences for CMV DNA were constructed by PCR amplification of the DNA using aminated primer as described by Zammatteo et al. (Anal. Biochem., 253, pp. 180–189 (1997)). The primers were purchased from Eurogentec (Liège, Belgium). Quantification of the amplicons was done by their absorption at 260 nm.

For the grafting on glass, a solution of aminated amplicons at 0.2 μm in MES 0.1 M pH 6.5 was first heated at 100° C. for 5 min and then spotted by a robot using 250 μm diameter pins (Genetix, UK). After incubation of 1 h at 20° C., they were washed with SDS solution at 0.1% and then two times with water. They were then incubated with NaBH$_4$ at 2.5 mg/ml solution for 5 min then washed in water and heated at 95° C. for 3 min before being dried.

Hybridisation of the Target Molecule

The target molecule was obtained by amplification by PCR in the presence of biotinylated dUTP at 1 mM (Alexandre et al., Biotechniques, 25, pp. 676–683 (1998)). Plasmids containing the sequence of CMV virus were used for the PCR. After amplification, the PCR products were purified using a kit of high pure PCR product purification (Boehringer, Mannheim, Germany) and quantified by ethidium bromide staining after separation on a 2% agarose gel.

For the hybridisation, various concentrations 0.67, 6.7 and 67 fm in 5 μl of biotinylated target DNA were added in a SSC 2× Denhard solution containing 20 μg of Salmon DNA. A drop of this solution (5 μl) was added on the array and incubated for 2 h at 65° C. in a wet atmosphere. The array was then washed 4 times with a maleic acid buffer 10 mM pH 7.5, containing NaCl 15 mM and Tween 0.1%.

Silver Precipitation on the Array After Silver Precipitation

The array was first incubated for 45 min with 0.8 ml of a streptavidin-colloidal gold (Sigma) diluted 1,000 times in a maleic buffer 150 mM pH 7.4 containing NaCl 100 mM and 0.1% dry milk ponder. The arrays were then washed 5 times 2 min in the maleic acid buffer 10 mM pH 7.4 containing 15 mM NaCl and Tween 0.1%. A "silver enhancement reagent" (40 μl) from Sigma was added onto the array and changed after 10 and then 5 min. After washing in the maleic buffer, the array was dried.

Detection and Analysis of the Array

The array was scanned and the digitalised image was treated with form recognition software in order to delimitate and identify the spots. The level of the pixels of each spot was integrated and a value given to each spot. The values were corrected for the background obtained in three places where no capture nucleotide sequences have been fixed.

EXAMPLE 2

Detection of Proteins on Biochips

Fixation of Antibodies on the Array

The glass of the array was activated as described here above in order to obtain aldehyde groups on the surface. The antibodies used in this experiment were raised against bovine serum albumin for positive control and non specific IgG for negative control. The antibodies at 10 μg/ml in PBS solution were spotted using the 250 μm diameter pins directly on the glass. The amino groups of the antibodies could react with the aldehyde present on the glass. The reaction was performed for 1 h at room temperature. The glasses were washed with a PBS buffer.

Detection of Bovine Serum Albumin by ELISA on the Array

A solution of bovine serum albumin (BSA) at 10 μμg/ml in PBS containing 0.1% casein was added on the array and incubated for 30 min. The array was then washed 3 times with PBS containing 0.1% Tween 20 and then incubated with a solution of biotinylated anti-BSA at 20 μg/ml in PBS containing 0.1% casein. The incubation was performed for 30 min. A streptavidin-Gold complex at 1 μg/ml was then incubated for 30 min in a PBS solution containing 0.1% casein. The presence of gold served as a center for silver reduction. The silver precipitation was performed with a "silver enhancement reagent" from Sigma with a change of the solution after 10 min and then again after 5 min. The glasses were then scanned and the data analysed as presented in the example here above.

EXAMPLE 3

Figure 2:
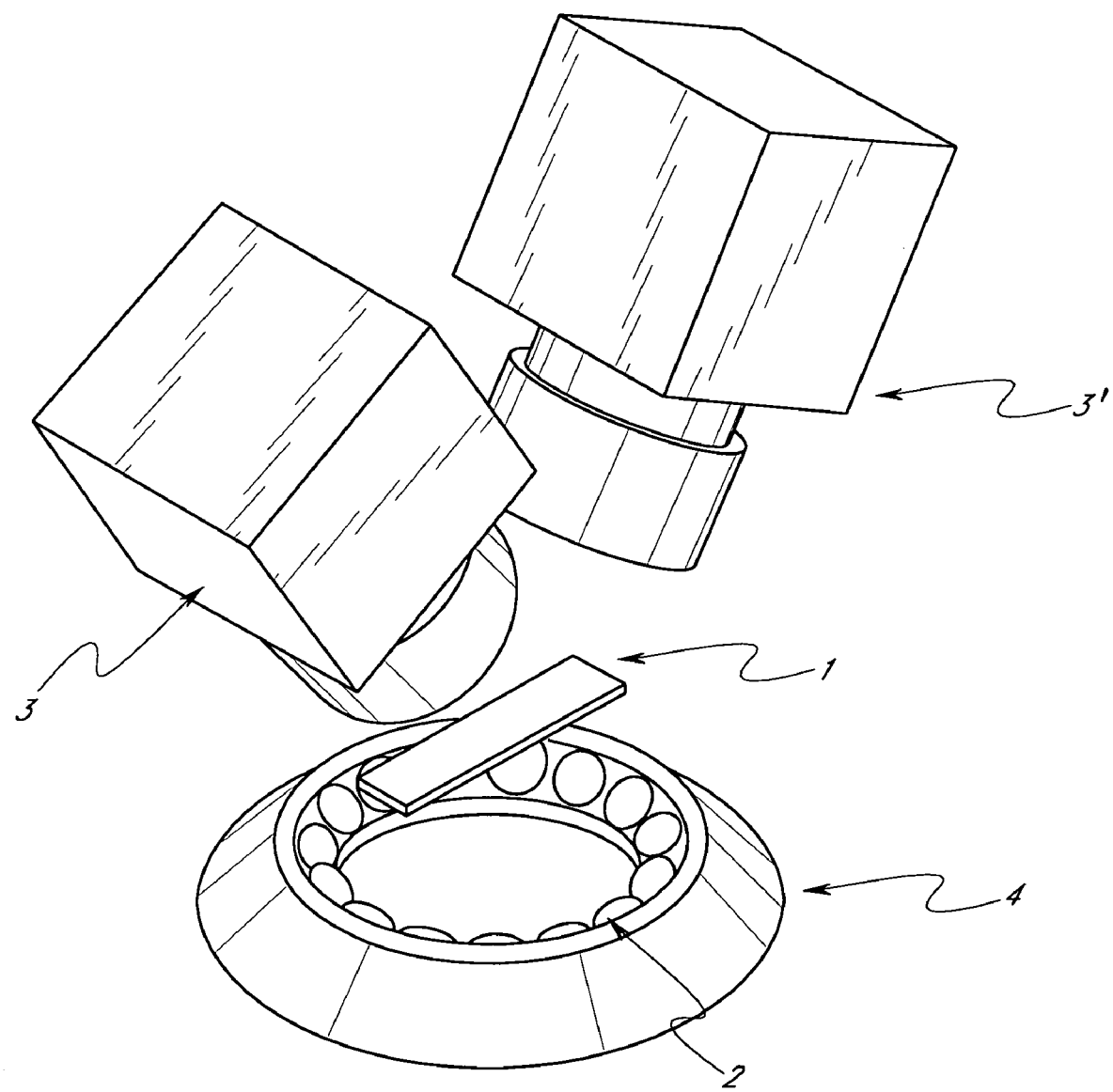
FIG. 2 represents an embodiment of the apparatus comprising a solid support 1 above several regularly spaced illuminant sources 2 on a circular support 4 and two cameras 3, 3' placed above the solid support.
Figure 3:
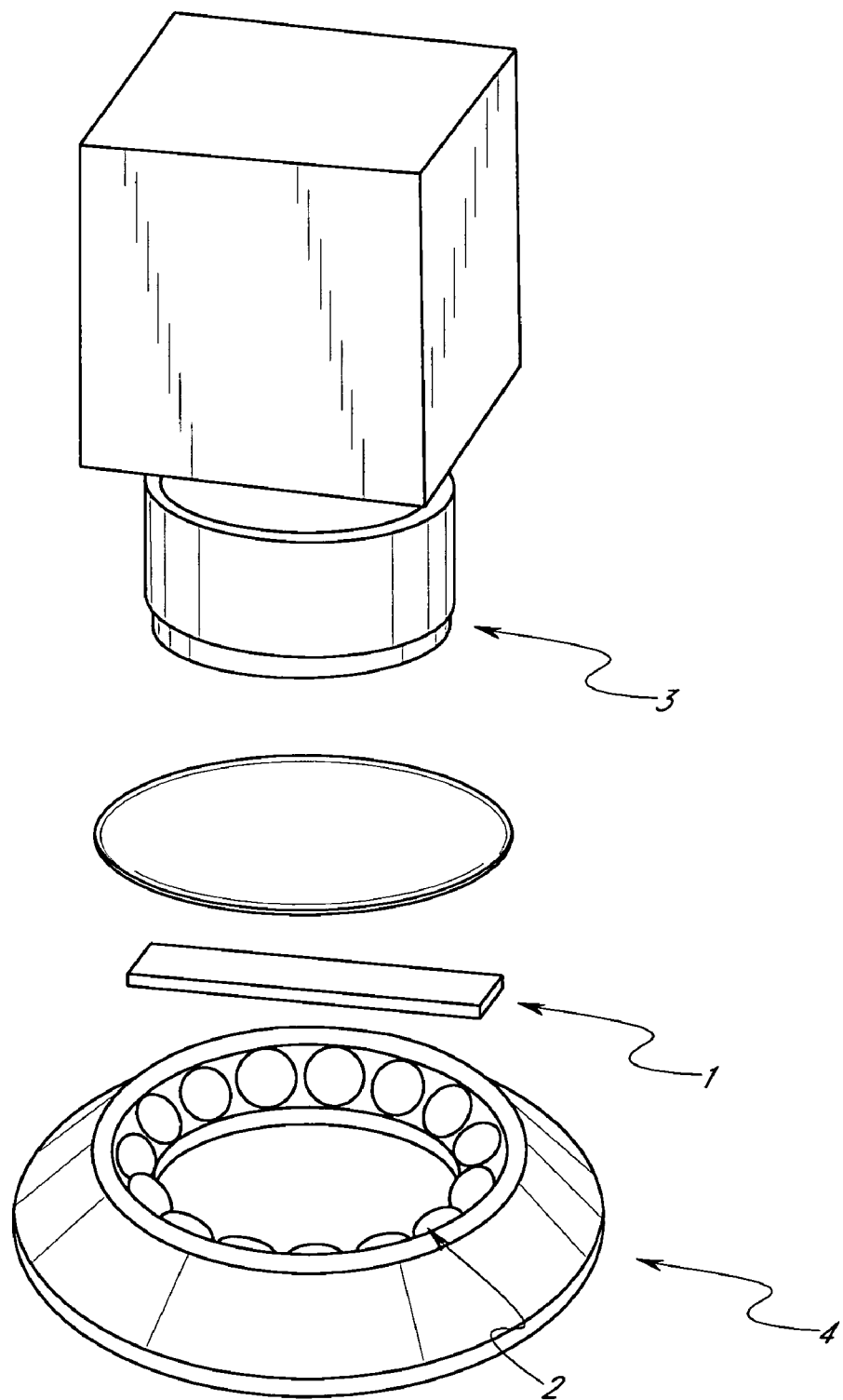
FIG. 3 represents an embodiment of the apparatus comprising a solid support 1, above several regularly spaced illuminant sources 2 on a circular support 4 and a single camera 3 placed above the solid support.
Figure 4:
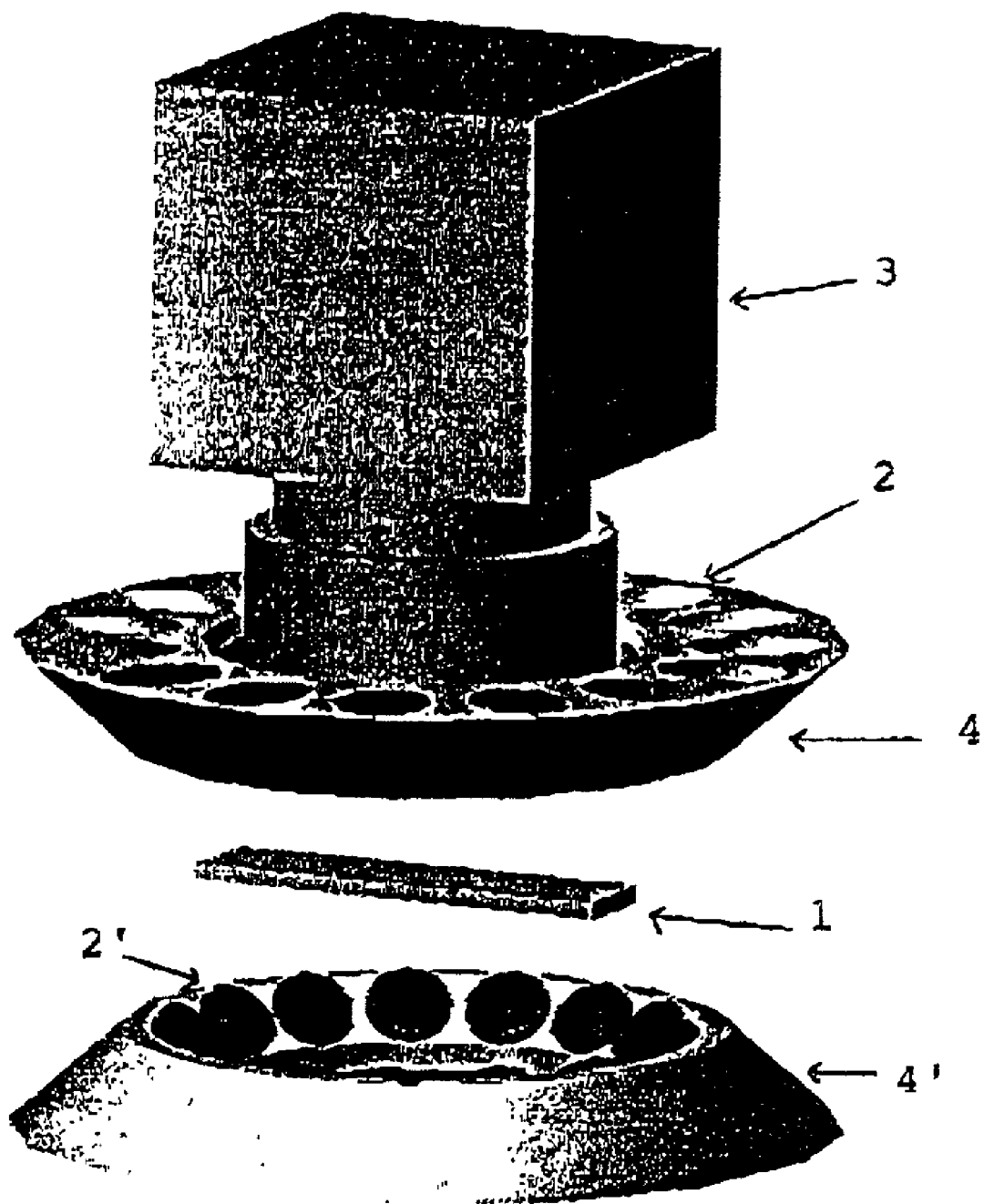
FIG. 4 represents an embodiment of the apparatus comprising two regularly spaced illuminant sources 2, 2', each on a circular support 4, 4'. The first set of sources 2 is placed above the solid support 1 and the second set of sources 2' is placed below the solid support. Both sets of illuminant sources are symmetrical to the solid support and a camera 3 is placed above the first illuminant source set.
Figure 5:
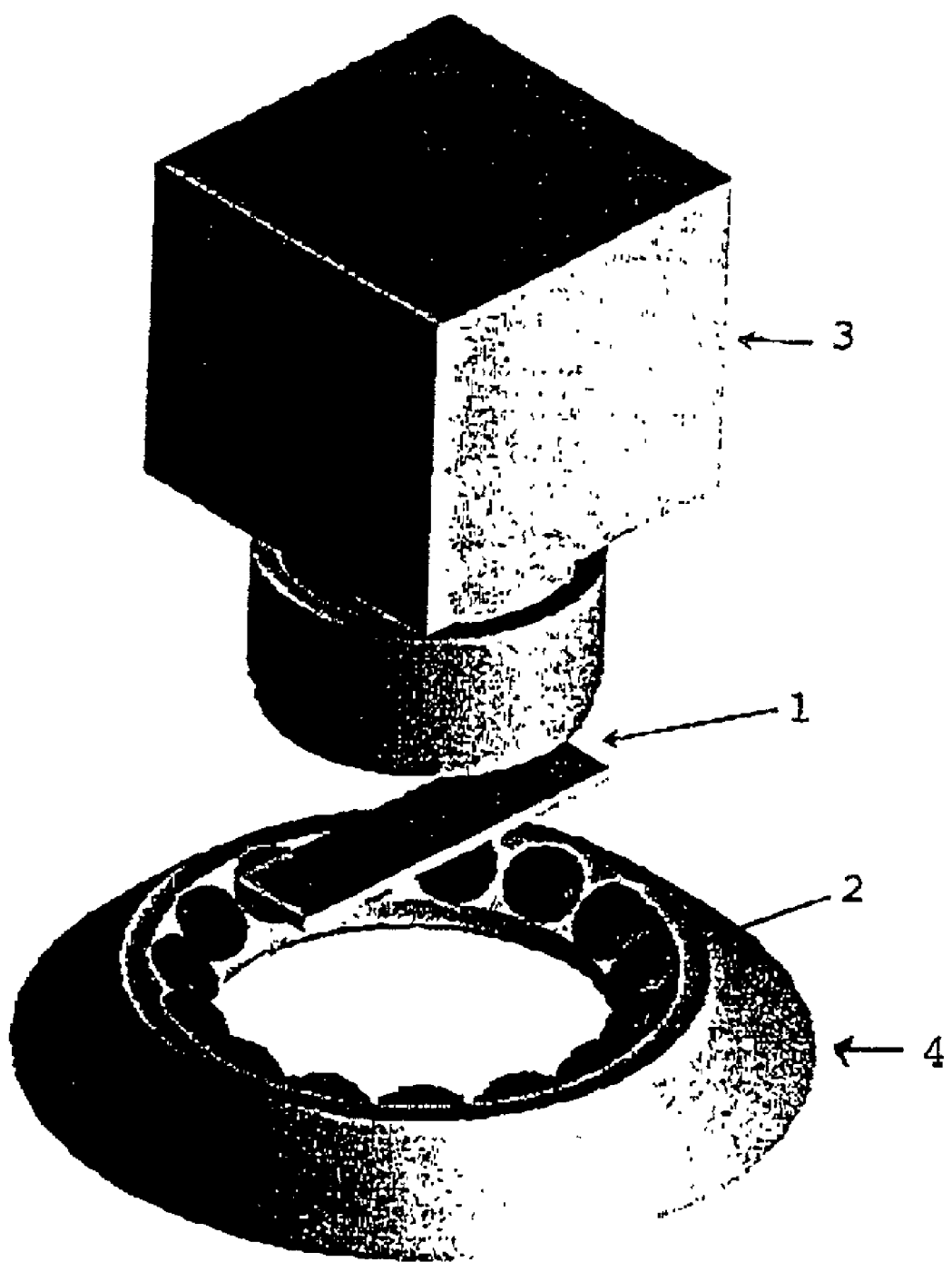
FIG. 5 represents an embodiment of the apparatus comprising a solid support 1 above the illuminant sources 2 which may or may not be regularly spaced from each other on a circular support 4. The camera 3 is placed above the solid support.
Figure 6:
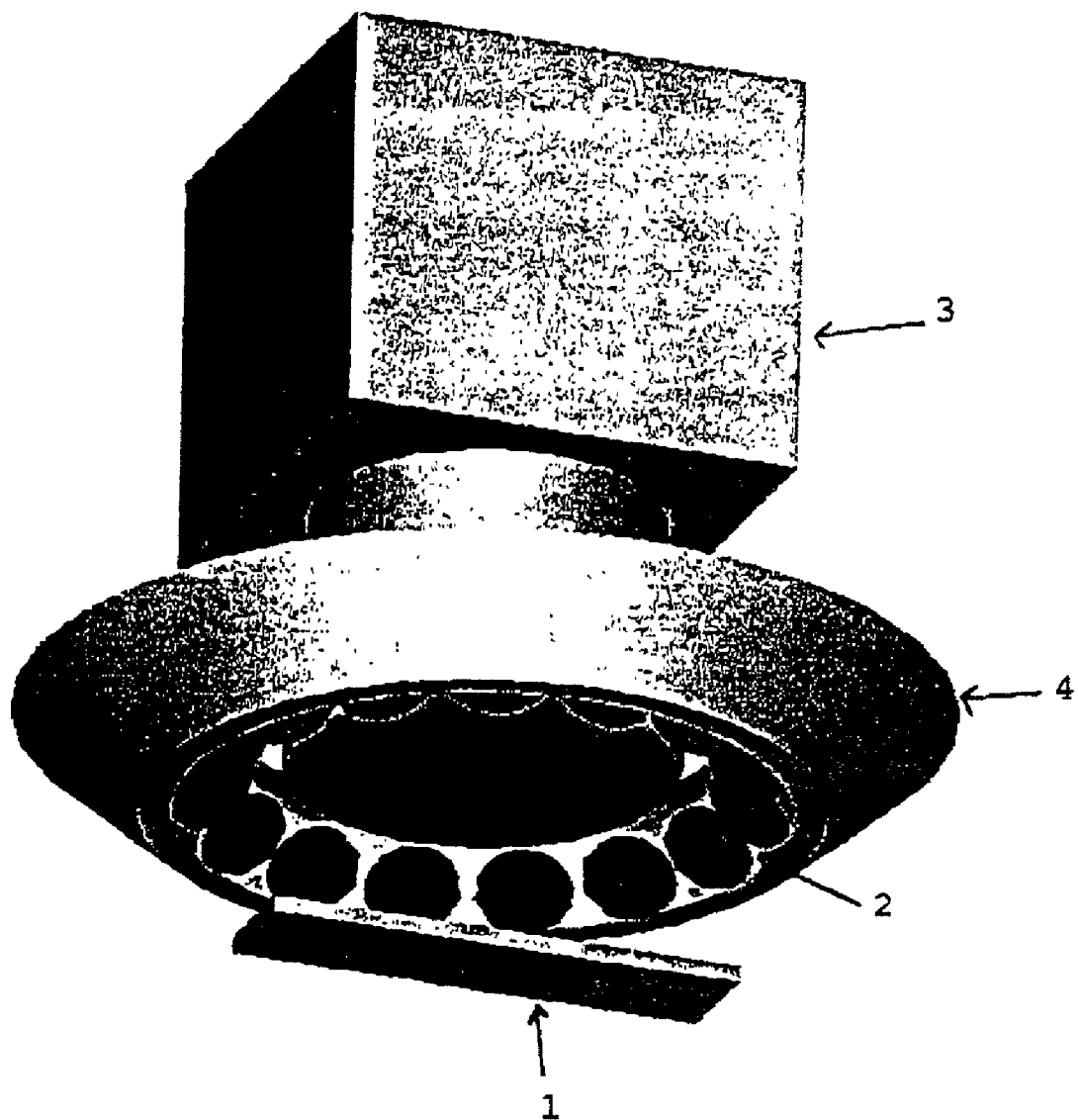
FIG. 6 represents the camera 3 above the first illuminant source 2 on a circular support 4 as described in FIG. 4. Both the camera and the illuminant source are above the solid support 1.
Figure 7:
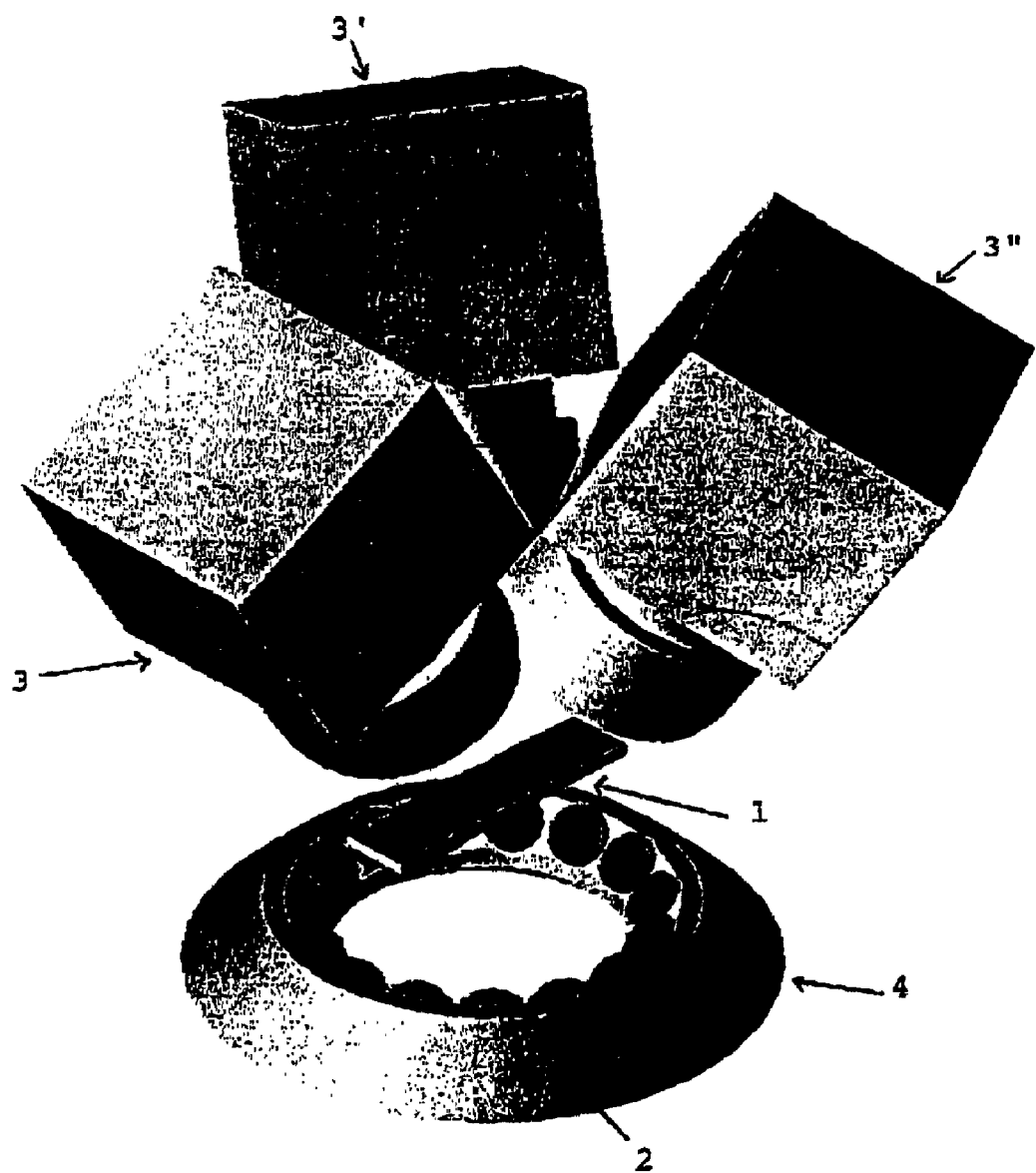
FIG. 7 represents an embodiment of the apparatus comprising several regularly spaced illuminant sources 2 on a circular support below the solid support 1. Above the solid support are three cameras 3, 3', 3" in a triangular arrangement.

Preferred embodiments of the apparatus for performing the quantification method according to the invention is shown in the FIGS. 2 to 7. The apparatus comprises a solid support 1, several illuminant sources 2 regularly spaced from each other on a circular support 4, said circular support being placed under said solid support 1, and two cameras 3, 3', said cameras being placed above said solid support 1 and being arranged oppositely in a plane.

The apparatus may also comprise a solid support 1, several illuminant sources 2 regularly spaced from each other on a circular support 4, said circular support being placed under said solid support 1, and one camera 3 placed above said solid support 1.

Further, the apparatus may also comprise a solid support 1. The apparatus comprises also a first set of illuminant sources 2 and a second set of illuminant sources 2, the illuminant sources of each set 2, 2' being regularly spaced from each other in a plane, preferably on a circular support 4, 4'. The first set of illuminant sources 2 is placed above the solid support 1 and the second set 2' is placed under said solid support 1, said first and said second sets of illuminant sources 2, 2' being placed symmetrically according to the position of said solid support 1. The apparatus also comprises a camera 3 placed above said solid support 1 and above the first set of illuminant sources 2.

Further, the apparatus may also comprise a solid support 1, with or without several illuminant sources 2 being regularly spaced from each other in a plane, preferably on a circular support 4, and being placed under the solid support 1. The apparatus comprises also a camera 3 placed above. Said circular support 4 and said camera 3 are placed symmetrically according to the position of the solid support 1.

Finally, the apparatus may also comprise a solid support 1 with several illuminant sources 2 regularly spaced from each other in a plane, preferably on a circular support 4, said circular support being placed under said solid support 1, and three cameras 3, 3', 3", said cameras being placed above said solid support 1 and being arranged according to triangular arrangement in a plane.

What is claimed is:

1. A method for the identification and/or the quantification of a target compound obtained from a sample, comprising the steps of:
   putting into contact the target compound with a capture molecule in order to allow a specific binding between said target compound with said capture molecule, said capture molecule being fixed upon a surface of a solid support according to an array comprising discrete regions with a density of at least 20 of said discrete regions per $cm^2$, each of said discrete regions being fixed with one species of capture molecules;
   performing a catalytic reduction of a metal present in solution leading to formation of a metallic precipitate in one or more of said discrete regions;
   determining the possible presence and quantification of precipitate(s) in said discrete region(s); and correlating the presence and quantification of the precipitate(s) at the discrete region(s) with the identification and/or a quantification of said target compound.

2. The method according to claim 1, wherein said metallic precipitate is a magnetic metallic compound.

3. The method according to claim 1, wherein the catalytic reduction leading to the formation of the metallic precipitate is a reduction of a metal in the presence of an enzyme.

4. The method according to claim 1, wherein the catalytic reduction leading to the formation of the metallic precipitate is a chemical reduction of silver in the presence of colloidal gold particles coupled to the bound target compound.

5. The method according to claim 1, wherein the specific binding between the target compound and its corresponding capture molecule is a hybridization between two nucleotide sequences.

6. The method according to claim 1, wherein the binding between the target compound and its corresponding capture molecule is a reaction between an antigenic structure and its corresponding antibody or a hypervariable portion thereof.

7. The method according to claim 1, wherein the binding between the target compound and its corresponding capture molecule is a reaction between a receptor and its corresponding ligand.

8. The method according to claim 1, wherein the possible presence and quantification of a precipitate is obtained by reflection, absorption or diffusion of a light beam upon said precipitate.

9. The method of claim 8, wherein the light beam is a laser beam.

10. The method according to claim 1, wherein the presence and quantification of a precipitate in a discrete region is obtained by variation of an electromagnetic field or the conductance of an electric current.

11. The method according to claim 1, for the quantification of volume of one or more precipitate(s) upon a defined surface of the solid support, wherein images of said defined surface containing one or more precipitate(s) and corresponding to different views, said images containing analogue information, are taken by one or more camera(s) upon illumination by one or more illuminant source(s), spatially arranged relatively to each other according to a predetermined pattern and wherein the corresponding image analogue information of said defined surface containing said precipitate(s) are transformed and converted into digital form or a set of digital forms and compared to a first and to a second reference standards to determine the volume of the precipitate(s) to be quantified.

12. The method according to claim 11, wherein the first reference standard corresponds to a digital form or a set of digital forms obtained from analogue information contained in images taken on the surface of said solid support without precipitate.

13. The method according to claim 12, wherein the second reference standard corresponds to a digital form or a set of digital forms obtained from analogue information contained in images taken on the surface of said solid support containing precipitate(s) of known volume.

14. The method of claim 1, wherein said metallic precipitate is formed on the surface of a particle associated with said target compound.

15. The method of claim 1, wherein said sample is a biological sample.

16. A diagnostic and/or quantification apparatus comprising:
   a solid support comprising an array comprising at least 20 discrete regions per $cm^2$ comprising multiple species of capture molecules, each of said discrete regions being fixed with one species of capture molecule which recognizes a target compound, wherein binding of said target compound to one or more of said multiple species of capture molecules leads to a catalytic reduction of a metal present in solution, and a formation of a metallic precipitate in one or more of said discrete region(s);

a detection and quantification device for detecting and quantifying said precipitate in said discrete region(s); and a computer programmed to collect the results obtained from said detection and quantification device.

17. The apparatus according to claim 16, comprising one or more sensor(s) provided with camera(s) and with one or more illuminant source(s) which are spatially arranged relatively to each other according to a predetermined pattern and which are associated with an analogue information acquisition system, said information being measured by using sensor(s) and being converted into digital form by a processing unit.

18. The apparatus according to claim 17, wherein the camera(s) are CCD or CMOS camera(s).

19. The apparatus according to claim 17, wherein the illuminant source is an infra-red light having a wavelength similar to a metal crystal contained in the precipitate(s).

20. The apparatus according to claim 17, which comprises a set of illuminant sources regularly spaced from each other in a plane, each of said sources corresponding to a light spot being automatically switched on, simultaneously or successively.

21. The apparatus according to claim 17, which comprises one camera and one illuminant source placed above the solid support, said camera and illuminant source being movable in three dimensions in space.

22. The apparatus according to claim 17, which comprises two or more cameras oppositely arranged in a plane and placed above the solid support, the apparatus comprising further one or more illuminant source(s) placed under the solid support.

23. The apparatus according to claim 17, which comprises three or more cameras arranged according to a triangular plane or another regular or irregular pattern and placed above the solid support and further comprising one or more illuminant source(s) placed under the solid support.

24. The apparatus according to claim 17, which comprises, placed above the solid support, one camera and a first illuminant source and, under said camera, a second illuminant source placed under the solid support, the two illuminant sources being placed almost symmetrically according to the position of the solid support.

25. The apparatus of claim 16, wherein the information(s) recorded upon said solid support are barcodes.

26. The apparatus of claim 16, wherein the results are the formation of a precipitate at a specific location.

27. The apparatus of claim 16, further comprising a device for reading information recorded upon said solid support.

28. The apparatus of claim 27, wherein said device for reading information comprises a bar code reader.

29. The apparatus of claim 16 wherein said computer is programmed to recognize discrete regions bearing said capture molecules.

30. The apparatus of claim 16, wherein said computer is programmed to detect and/or quantitate said target compounds.

31. A computer comprising program code stored thereon for performing the steps of determining the possible presence and quantification of a precipitate in discrete regions and correlating the presence and quantification of said precipitate at the discrete regions with the identification and/or the quantification of a target compound, according to the method of claim 1, when said program code is run on said computer.

32. A computer program product comprising program code means stored on a computer readable medium for performing the steps of determining the possible presence and quantification of a precipitate in a discrete region and correlating the presence and quantification of the precipitate at the discrete region with the identification and/or the quantification of a target compound, according to the method of claim 1, when said program is run on a computer.

* * * * *